United States Patent [19]

Stein et al.

[11] 4,241,185
[45] Dec. 23, 1980

[54] METHOD OF STABILIZING α-GALACTOSIDASE

[75] Inventors: Brooks M. Stein, Berthoud; James C. Linden, Loveland, both of Colo.

[73] Assignee: The Great Western Sugar Company, Denver, Colo.

[21] Appl. No.: 14,579

[22] Filed: Feb. 23, 1979

[51] Int. Cl.³ .......................... C12N 9/96; C12N 9/40
[52] U.S. Cl. ...................................... 435/188; 435/99; 435/174; 435/208
[58] Field of Search ................... 435/94, 99, 176, 174, 435/177, 182, 188, 276, 911, 208

[56] References Cited

U.S. PATENT DOCUMENTS

| | | | |
|---|---|---|---|
| 3,647,625 | 3/1972 | Suzuki et al. | 435/276 |
| 3,666,627 | 5/1972 | Messing | 435/176 |
| 3,779,869 | 12/1973 | Zienty | 435/174 |
| 3,843,442 | 10/1974 | Moskowitz | 435/94 |
| 3,957,580 | 5/1976 | Nelson | 435/174 X |

*Primary Examiner*—David M. Naff
*Attorney, Agent, or Firm*—Dennis K. Shelton; Bruce G. Klaas

[57] ABSTRACT

The activity of mycelial bound α-galactosidase is stabilized by treating α-galactosidase containing mycelia with about 5 to about 25 percent by weight glutaraldehyde based upon the dry weight of the mycelia. The glutaraldehyde treated mycelia may be used in the hydrolysis of oligosaccharides containing α-galactoside linkage without incurring substantial α-galactosidase activity loss during hydrolysis.

5 Claims, No Drawings

METHOD OF STABILIZING α-GALACTOSIDASE

BACKGROUND AND SUMMARY

This invention relates to the hydrolysis of oligosaccharides containing α-galactoside linkage in the presence of α-galactosidase and more particularly to a method for stabilizing α-galactosidase enzyme activity containing mycelia for subsequent use in the hydrolysis of oligosaccharides containing α-galactoside linkage.

The hydrolysis of oligosaccharides containing α-galactoside linkage, such as raffinose, stachyose, melibiose, galactobiose, verbascose, and the like, in the presence of α-galactosidase is an important commercial practice in some industries. For example, in the production of crystalline sugar from sugar beets, the naturally occurring trisaccharide raffinose is known to be present in sugar beet diffusion juice in varying quantities. Since raffinose forms insoluble calcium saccharates, it is precipitated together with sucrose in the conventional Steffen process, and tends to build up in Steffen molasses as sucrose is precipitated from the molasses solution. As with other impurities, the presence of raffinose in sucrose containing liquids detrimentally effects sucrose crystalization, such as by depressing the sucrose crystallization velocity and by resulting in the formation of cubic, flat or needle-like crystals at varying raffinose concentrations. In the past, it has been a common commercial practice to discard, or use merely as a by-product, molasses having a raffinose buildup of over about 5% by weight on dry substance without attempting to recover additional sucrose from the molasses. Such practices have resulted in the loss of substantial quantities of potentially recoverable sucrose.

To overcome the foregoing problems, it has previously been suggested to treat raffinose containing beet molasses with α-galactosidase to hydrolize the raffinose into D-galactose and sucrose, thereby permitting the recovery of additional sucrose from the molasses solution. For example, U.S. Pat. No. 3,647,625 of Suzuki et al relates to such a process wherein α-galactosidase is formed in mycelia of *Mortierella vinacea* var. raffinose-utilizer (ATCC No. 20034) to obtain mycelia substantially free of invertase activity. The foregoing α-galactosidase containing mycelia is commercially provided in pellet form to allow for continuous enzymatic treatment in a sucrose production process. Although this process has been successful in reducing the raffinose content of beet molasses and thereby increasing recoverable sucrose yields, it has been found that enzyme losses are relatively high due to actual physical loss of the mycelia, loss of α-galactosidase from the mycelia and/or inactivation of the α-galactosidase. Losses of each type substantially effect the realized enzyme activity level in a continuous raffinose hydrolysis process and the economic desirability of conducting such a process.

In addition, it has previously been known that glucose isomerase activity within whole *Streptomyces olivaceus* (NRRL 3583) bacterial cells can be stabilized by treating the whole bacterial cells with glutaraldehyde. See, for example, U.S. Pat. No. 3,779,869 of Zienty, which relates to such a process. However, there is no disclosure or suggestion in the Zienty patent that glutaraldehyde treatment might be effective for stabilization of anything other than glucose isomerase activity in whole bacterial cells.

In accordance with the present invention, it has been found that the α-galactosidase activity level in the hydrolysis of oligosaccharides containing α-galactoside linkage can be stabilized by treating mycelial bound α-galactosidase with about 5 to about 25 percent by weight glutaraldehyde based upon the dry weight of the mycelia. The treatment method is preferably performed by suspending α-galactosidase activity containing mycelia in an aqueous medium, adding an active site protection agent to the aqueous medium, adding the glutaraldehyde to the aqueous medium, maintaining the pH of the aqueous medium within the range of about 6.5 to about 8.5, mixing the aqueous medium for a period of at least about 0.25 hours, separating the mycelia from the aqueous medium and then washing the mycelia to remove excess glutaraldehyde. The treated α-galactosidase activity containing mycelia may then be used in a conventional manner in the hydrolysis of oligosaccharides containing α-galactoside linkage.

DESCRIPTION OF THE PRESENTLY PREFERRED EMBODIMENTS

The method of the present invention is useful for the treatment of mycelia containing α-galactosidase activity. Mycelia presently particularly preferred for use in the practice of the invention is mycelia of the mold *Montierella vinacea* var. raffinose-utilizer, or other α-galactosidase mycelia, which has been cultured in a manner so as to minimize invertase activity. An illustrative example of such mycelia is that available from the Agency of Industrial Science and Technology and the Hokkaido Sugar Company, Tokyo, Japan, under the tradename Melibia-D, an α-galactosidase containing mycelia of the mold *Montierella vinacea* var. raffinose-utilizer which is provided in dry pellet form.

In order to ensure uniform stabilization of the α-galactosidase enzyme, the mycelia is initially suspended in an aqueous medium having sufficient water content to permit uniform dispersion of the mycelia throughout the medium upon subsequent agitation. It has been found that about 5 liters of aqueous medium per kg. of mycelia is sufficient to adequately disperse the mycelia for further treatment.

In order to protect the α-galactosidase activity from potential detrimental effects of glutaraldehyde treatment, it is a presently preferred practice to add a sufficient amount of an active site protection agent to the medium to substantially decrease any such detrimental effects. Suitable active site protection agents include agents which will enter the active site of the α-galactosidase enzyme and prevent glutaraldehyde bridging across the active site thereby decreasing availability of the active site to raffinose or other oligosaccharide acceptance. Illustrative examples of suitable active site protection agents include raffinose, sucrose, melibiose, galactose, glucose and fructose. The presently particularly preferred active site protection agent is glucose. The active site protection agent is preferably added in a greater than stoichiometric amount relative to available enzyme active sites to ensure a high level of protection. When the active site protection agent is glucose, it has been found that about 1 to about 10, preferably about 2 to about 5, and more preferably about 2 to about 3 percent by weight glucose, based upon the dry weight of the mycelia, is effective for this purpose.

The mycelia-containing aqueous medium is then treated by adding about 5 to about 25, preferably about 7.5 to about 15, and more preferably about 9 to about 12 percent by weight glutaraldehyde, based upon the dry weight of the mycelia, to the dispersion. The pH of the dispersion is adjusted to about 6.5 to about 8.5, preferably about 7.5 to about 8.5, with a suitable pH adjusting agent, such as NaOH, and is then mixed for a sufficient time to obtain maximum glutaraldehyde stabilization, usually at least about 0.25 and more preferably at least about 1.0 hours. To obtain optimum results, the glutaraldehyde may be continuously added to the aqueous medium over the treatment period with frequency NaOH additions to maintain the desired pH levels.

During the mixing period, it is particularly critical to limit, and preferably to minimize, inclusion of atmospheric oxygen in the aqueous medium. It has been found that inclusion of relatively high levels of atmospheric oxygen results in an immediate decline or suppression of α-galactosidase activity. Mixing of the aqueous medium is therefore carried out in a manner so as to limit, and preferably to minimize, oxygen inclusion in the medium. For example, mixing may be accomplished by stirring the aqueous medium in a closed container having a layer of inert gas overlaying the aqueous medium, by gently agitating the aqueous medium or by other suitable means.

After mixing for sufficient time to obtain the desired degree of glutaraldehyde stabilization of the enzyme, the mycelia are separated from the dispersion, such as by settling and decantation, by filtration, by centrifugation, or by other suitable means. The mycelia are then washed to remove excess residual glutaraldehyde. Washing of the treated mycelia may be accomplished by resuspending the mycelia in an aqueous medium, such as tap water, distilled water or deionized water, followed by separation of the mycelia from the medium in a conventional manner. Preferably, the mycelia are washed at least twice to insure adequate excess glutaraldehyde removal prior to subsequent use of the mycelia. The washed, stabilized α-galactosidase containing mycelia are then ready to be used in a conventional process for the hydrolysis of oligosaccharides containing α-galactoside linkage.

The foregoing principles may be better understood in association with the following illustrative examples. As used in these examples, an activity unit is defined as the amount of enzyme required to liberate 1µg of glucose per hour at 50° C. from melibose at 30 Brix and a pH of 5.2.

EXAMPLE I 350 g. of dry, pelletized Melibia-D, an α-galactosidase activity containing mycelium obtained from the Hokkaido Sugar Company, Tokyo, Japan, is added to 2 liters (1.) of a 0.015 M aqueous solution of melibiose, and the resulting mixture is mixed for two hours at a temperature of 5° C. to protect the enzyme active sites of the α-galactosidase. The mixture is then divided into four equal samples. To each of the four samples is added the percentage of reagent grade glutaraldehyde shown in Table I, based upon the dry weight of the mycelia in the sample, to form four separate reaction mixtures. The pH of the reaction mixtures is maintained at 8.5 by the addition of NaOH, and the reaction mixtures are allowed to react under constant gentle agitation at 23° C. for one and one-half hours. The reaction mixtures are allowed to settle, and excess liquid is decanted from the settled mycelia. The mycelia are washed twice in 2 l. of deionized water, with supernatant wash water being decanted from the mycelia of each sample. Each sample is then added to 500 ml. of a 30 RDS molasses solution having a pH of 5.2 to form hydrolysis mixtures. 50 g. of sea sand is added to each hydrolysis mixture, and the hydrolysis mixtures are placed in a shaker bath at 50° C. After a two hour hydrolysis reaction period, no significant difference is apparent between the enzyme activities of the various hydrolysis mixtures. After three weeks, the α-galactosidase activities of the hydrolysis mixtures are as shown in TABLE I:

TABLE I

| Hydrolysis Mixture | % Glutaraldehyde | Activity (Units/g × 10³) 0 Weeks | 3 weeks | % of Initial Control |
|---|---|---|---|---|
| 1 | 0 | 839 | 86 | 10 |
| 2 | 0.1 | 842 | 108 | 13 |
| 3 | 1.0 | 853 | 104 | 12 |
| 4 | 10.0 | 831 | 378 | 45 |

EXAMPLE II

The procedure of Example I is repeated with the substitution of glucose for melibiose, at the glutaraldehyde treatment levels shown in Table II, and for a hydrolysis reaction time of two weeks. The α-galactosidase activities of the hydrolysis mixtures are as shown in TABLE II:

TABLE II

| Hydrolysis Mixture | % Glutaraldehyde | Activity Units/g × 10³ 0 Weeks | 1 Week | 2 Weeks | % of Initial Control Activity Remaining 1 Week | 2 Weeks |
|---|---|---|---|---|---|---|
| 1 | 0 | 1004 | 176 | 68 | 18 | 7 |
| 2 | 5 | 1339 | 428 | 316 | 43 | 32 |
| 3 | 10 | 1138 | 605 | 385 | 60 | 39 |
| 4 | 15 | 868 | 493 | 437 | 49 | 44 |

EXAMPLE III

The procedure of Example II is repeated without the addition of melibiose, glucose or any other active site protection agent at 0% and 10% glutaraldehyde treatment levels. The α-galactosidase activity levels of the hydrolysis mixtures are shown in TABLE III:

TABLE III

| Hydrolysis Mixture | % Glutaraldehyde | Activity Units/g × 10³ 0 Weeks | 1 Week | 2 Weeks | % of Initial Control Activity Remaining 1 Week | 2 Weeks |
|---|---|---|---|---|---|---|
| 1 | 0 | 1004 | 176 | 57 | 18 | 6 |
| 2 | 10 | 875 | 587 | 619 | 58 | 62 |

The data of Tables I, II and III illustrate that the α-galactosidase enzyme activity level of the mycelia is significantly stabilized by glutaraldehyde treatment, particularly at the 5%–15% glutaraldehyde treament levels, and that pre-treatment of the mycelia with an active site protection agent is effective in reducing initial enzyme activity losses incurred in the subsequent glutaraldehyde treament.

EXAMPLE IV

The procedure of Example II is followed with treatment in the glutaraldehyde reaction mixture for 0.25, 0.5, 1.0 and 2.0 hours. Similar results are obtained in the 0.5, 1.0 and 2.0 hour treatments, with a lesser degree of stabilization being obtained in the 0.25 hour treatment.

EXAMPLE V

The procedure of Example II is repeated while maintaining the pH of the glutaraldehyde reaction mixture at 6.5. Similar results are obtained.

While the invention has been described in association with certain presently preferred embodiments, certain modifications will be apparent to those skilled in the art. Such modifications are intended to be within the scope of the appended claims except as precluded by the prior art.

What is claimed is:

1. A method of stabilizing mycelial bound α-galactosidase activity comprising:
   (a) suspending mycelia of *Mortierella vinacea* var. raffinose-utilizer (ATCC No. 20034) containing α-galactosidase activity in an aqueous medium;
   (b) adding about 5 to about 25 percent by weight glutaraldehyde based upon the dry weight of the mycelia to the aqueous medium;
   (c) maintaining the pH of the aqueous medium at about 6.5 to about 8.5; and
   (d) mixing the aqueous medium in a manner so as to minimize oxygen inclusion for a period of about 0.25 to about 2.0 hours.

2. The method of claim 1 wherein about 7.5 to about 15 percent glutaraldehyde is added to the aqueous medium and the aqueous medium is mixed for about 0.5 to about 1.5 hours.

3. A method of stabilizing mycelial bound α-galactosidase activity, comprising:
   (a) suspending mycelia of *Mortierella vinacea* var. raffinose-utilizer (ATCC No. 20034) containing α-galactosidase activity in an aqueous medium;
   (b) adding about 1 to about 10 percent by weight of an active site protection agent, based upon the dry weight of the mycelia to the aqueous medium;
   (c) adding about 5 to about 25 percent by weight glutaraldehyde, based upon the dry weight of the mycelia, to the aqueous medium;
   (d) maintaining the pH of the aqueous medium at about 6.5 to about 8.5;
   (e) mixing the aqueous medium in a manner so as to minimize oxygen inclusion for a period of about 0.25 to about 2.0 hours;
   (f) separating the mycelia from the aqueous medium; and then
   (g) washing the mycelia to remove excess glutaraldehyde.

4. The method of claim 3 wherein the active site protection agent is selected from the group consisting of galactose, sucrose, melibiose, fructose, glucose and raffinose.

5. The method of claims 3 or 4 wherein about 7.5 to about 15 percent gluteraldehyde is added to the aqueous medium.

* * * * *